United States Patent [19]

Lary

[11] 4,273,128
[45] Jun. 16, 1981

[54] CORONARY CUTTING AND DILATING INSTRUMENT

[76] Inventor: Banning G. Lary, 6225 SW. 117th Ter., Miami, Fla. 33156

[21] Appl. No.: 111,807

[22] Filed: Jan. 14, 1980

[51] Int. Cl.³ .................... A61B 17/32; A61M 29/02
[52] U.S. Cl. .................................. 128/305; 128/344
[58] Field of Search .......... 128/305, 325, 344, 349 B, 128/349 BV, 303 R, 348, 751, 752, 304

[56] References Cited

U.S. PATENT DOCUMENTS

| | | | |
|---|---|---|---|
| 2,730,101 | 1/1956 | Hoffman | 128/305 |
| 3,336,927 | 8/1967 | Klebanoff | 128/305 |
| 3,435,826 | 4/1969 | Fogarty | 128/344 X |
| 3,506,010 | 4/1970 | Murr | 128/276 |

FOREIGN PATENT DOCUMENTS

| | | | |
|---|---|---|---|
| 2804015 | 8/1979 | Fed. Rep. of Germany | 128/305 |
| 548303 | 9/1956 | Italy | 128/305 |

*Primary Examiner*—Stephen C. Pellegrino
*Assistant Examiner*—Michael H. Thaler
*Attorney, Agent, or Firm*—Ernest H. Schmidt

[57] ABSTRACT

A surgical instrument for the treatment of stenotic and occlusive coronary artery disease is described whereby the lumen of the coronary artery is longitudinally incised sub-epicardially through an area of narrowing or obstruction immediately whereafter dilation of the arterial lumen at the site of the stenotic blockage and arterial incision is effected by expansion under pressure of a balloon passed to the site through the artery. This coronary artery cutting and dilating instrument has a flexible probe at the distal end for guidance through the coronary artery, followed, in succession, by one or more radially extending knife blades for making the coronary incision and an inflatable balloon for dilating the stenotic artery zone immediately after the incision. A flexible inflating and control tube extends from the balloon to the proximal end, whereat a surgical syringe is connectable to effect hydraulic inflation of the balloon. The proximal tubular extension of the instrument is either short for use in exposed heart surgery on the beating heart by passage through the coronary artery beneath a purse-string incision made in the epicardium overlying the affected artery within a few centimeters from the blockage, or comparatively long for application through a catheter introduced via a peripheral artery.

6 Claims, 10 Drawing Figures

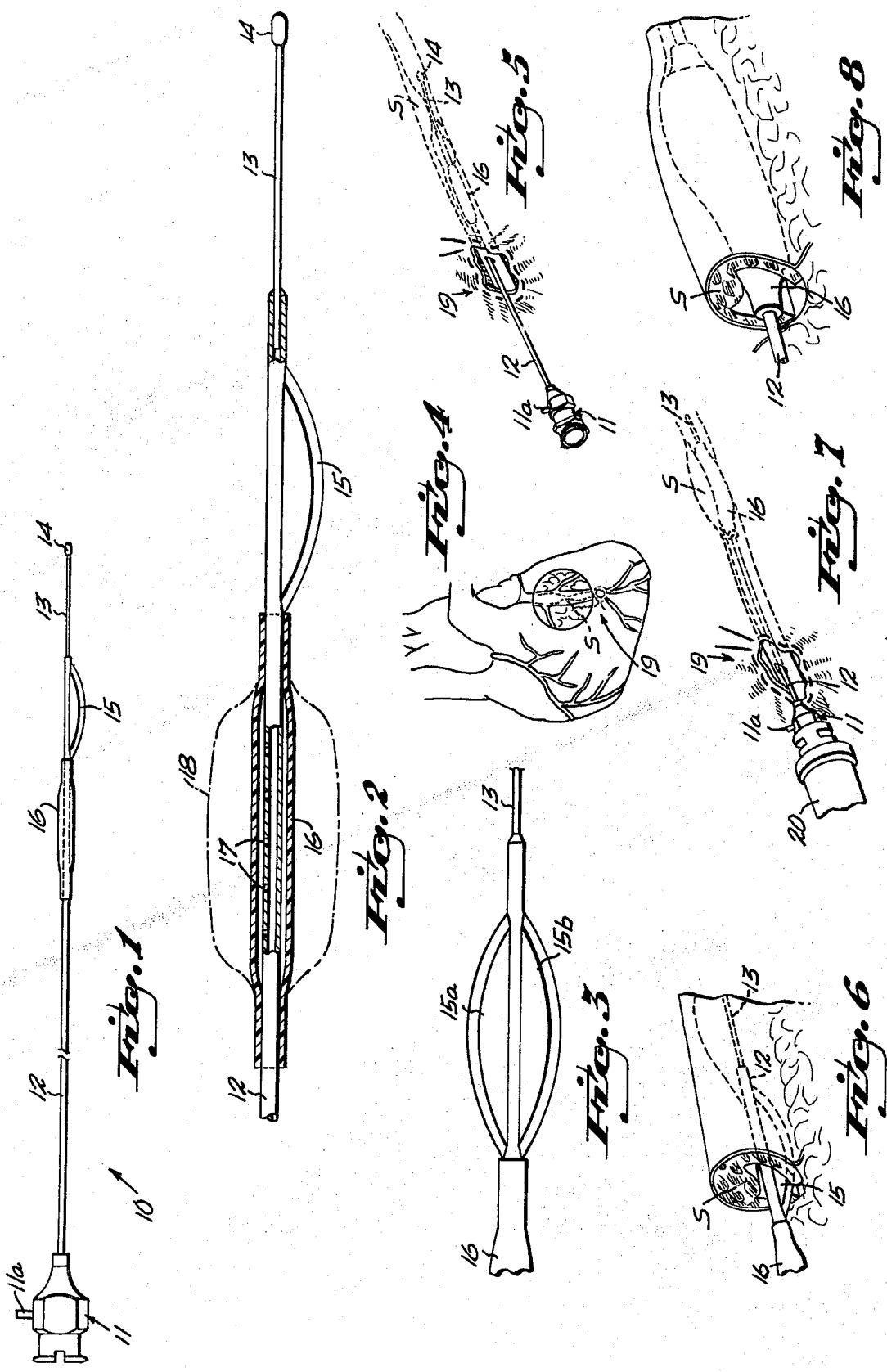

CORONARY CUTTING AND DILATING INSTRUMENT

BACKGROUND OF THE INVENTION

This invention relates generally to coronary artery surgery and is directed particularly to an improved method and means for the surgical treatment of stenotic or occluded major coronary vessels while the heart is beating and without the use of the heart and lung machine, although it can also be used with these modalities with the heart in fibrillation or arrest.

In recent years occlusive coronary artery disease has been surgically treated with the use of various artery by-pass techniques involving cardiopulmonary by-pass. Although these techniques have been highly successful and can be performed with minimal risk, the unusual surgical skill required, and the complexity of the procedure, limits the operation to a small percentage of those patients who could otherwise be benefited. In attempts to surgically treat the vast number of coronary artery disease patients to whom the usual open heart coronary artery by-pass operation was not available or otherwise not indicated, various surgical techniques have heretofore been devised to effect myo-cardial revascularization and neo-vascularization. These procedures can be performed on the beating heart without cardio-pulmonary by-pass, thereby greatly simplifying the procedure with an attendant lessening of the risk. These new techniques, moreover, have been greatly advanced by the comparatively recent development of cine-coronary arteriography.

Most promising of the new surgical techniques has been the direct approach to increase the diameter of the coronary arteries narrowed or obstructed by the disease. One technique involves longitudinal incision of the myo-cardial side of the coronary artery at the site of the stenosis or occlusion, with the insertion of a scalpel through a small incision made in the wall of the coronary artery distal to the occlusion. This procedure effects an immediate increase in the size of the lumen for restored blood flow, but in the calcific rigid artery the lumen may remain small. Upon healing, the inside myocardial tissue assumes an intima-like surface defining, with the contiguous decompressed arterial zone, a new lumen having an approximately normal diameter.

In another of the new surgical techniques, known as percutaneous translumenal coronary angioplasty, an inflatable balloon carried at the end of a catheter or the like is passed through the affected artery to the site of the stenosis as observed in cine-coronary arteriography, and then inflated to compact the stenonic plaque and thereby increase the lumen size by dilation. A distinct advantage of this technique is that the catheter can be inserted through a peripheral artery, thereby obviating surgical opening of the chest wall to expose the heart. This technique, however, has limited application because of major problems in its use in the treatment of stenoses associated with coronary artery rigidity, obstruction, and with single severe and multiple stenoses.

SUMMARY OF THE INVENTION

It has been found that a combination of the above-described direct approach surgical techniques of longitudinal incision of the sub-epicardial portion of the coronary artery, together with immediately subsequent dilation thereat, will open the lumen and permit it to remain open without damaging or otherwise comprising the myo-cardium, and that this can be accomplished expeditiously and with minimal risk by the use of improved instrumentation comprising the invention. This new combinative technique not only may obviate the use of the heart-lung machine assist, but also permits immediate and permanent enlargement of the lumen of the artery, resulting in increased blood flow to the myocardium.

It is, accordingly, the principal object of this invention to provide a novel and improved coronary artery incision and dilation instrument that allows for both cutting and immediately successive dilation of the coronary artery from within the lumen of the vessel.

Another object of the invention is to provide a surgical instrument of the character described which is adaptable for surgical use either at the site of the coronary artery after opening of the chest wall, or which, in appropriate cases, can be combined with a catheter for introduction to the coronary artery site through a peripheral artery without the necessity for opening the chest wall.

Other objects, features and advantages of the invention will be apparent from the following description when read with reference to the accompanying drawings.

BRIEF DESCRIPTION OF THE DRAWINGS

In the drawings, wherein like reference numerals denote corresponding parts throughout the several views:

FIG. 1 is a side view of a coronary artery cutting and dilating instrument embodying the invention;

FIG. 2 is a fragmentary enlarged view of the cutting knife and dilating balloon portion of the instrument illustrated in FIG. 1, with portions broken away to illustrate constructional details;

FIG. 3 is a partial side view of the instrument as illustrated in FIG. 2, but showing a modified form thereof wherein a pair of diametrically opposed cutting blades are used instead of a single blade;

FIG. 4 illustrates pictorially a human heart with a magnified zone showing a typical stenosis in the anterior descending coronary artery;

FIG. 5 illustrates how the coronary artery cutting and dilating instrument, in use, is passed through a purse-string sutured cut in the coronary artery to approach the stenosis from the distal side;

FIG. 6 illustrates a fragmentary cross-sectional view of the stenonic zone of the artery illustrated in FIG. 5 showing the cutting of the arterial wall extending into the peri-arterial tissues;

FIG. 7 illustrates how deeper insertion of the instrument places the balloon section at the site of the stenotic constriction just prior to inflation;

FIG. 8 illustrates, on an enlarged scale as compared with FIG. 7, how inflation of the balloon serves to dilate and spread the incised stenonic artery zone to enlarge its lumen;

DESCRIPTION OF THE PREFERRED EMBODIMENT

Figure 9:
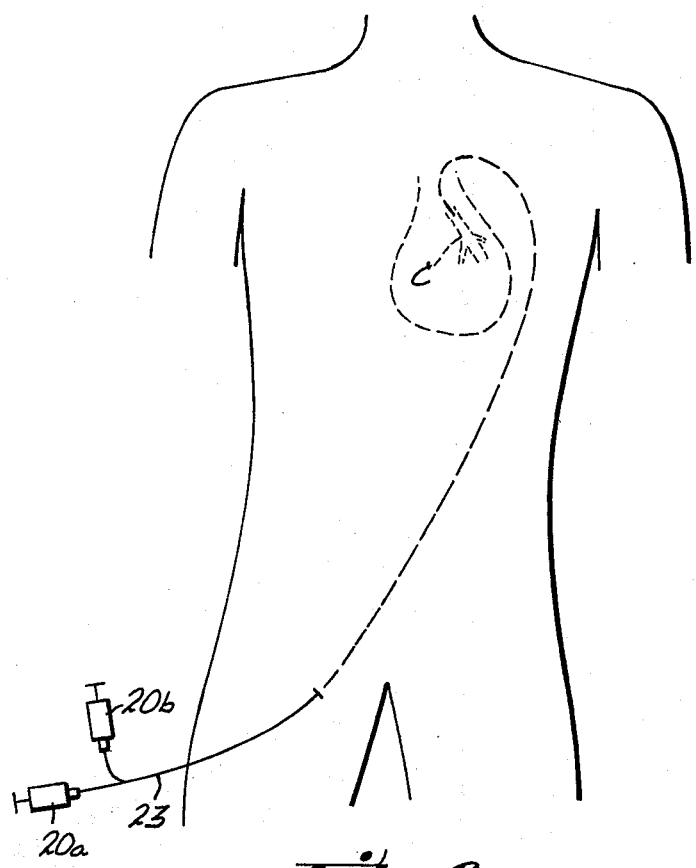
FIG. 9 illustrates, schematically, how a coronary cutting and dilating instrument comprising the invention can be combined with a catheter introduced through a peripheral artery for performing the surgical procedure without the necessity for opening the chest wall.

Referring now in detail to the drawings, reference numeral 10 designates one form of coronary artery cutting and dilating instrument embodying the invention. The instrument 10 comprises a standard vacuum syringe connector fitting device 11 at one end, communicating with a slightly flexible length of tubing or cannula 12, the distal end of which has secured thereto a coaxial, outwardly-extending, flexible wire probe member 13 terminating in a blunt, ovoid tip 14 of increased diametric size. The probe wire 13 will preferably be secured to the cannula 12 by having a short, proximal end portion telescopically received within said cannula and soldered or welded in place, thereby blocking the tubing opening. Welded, soldered or otherwise securely affixed at the distal end of the cannula 12, and extending radially outward thereof, is an arcuate knife blade 15. Circumjacently fitted on the cannula 12, directly behind the knife blade 15, is an elongated balloon member 16, the ends thereof being circumjacently secured to said cannula by a suitable cement, and/or an outer wrapping or a suitably thin wire or plastic filament (not illustrated).

As illustrated in FIG. 2, the cannula 12, along that portion within the elongated balloon member 16, is provided with a plurality of side wall through openings or apertures 17 through which balloon inflating fluid can flow as controlled by use of an inflating syringe during use of the instrument, as is hereinbelow more particularly described. In FIG. 2 the normal, collapsed condition of the expansible balloon 16 is illustrated by full-line representation thereof, whereas the "inflated" condition thereof is illustrated in broken lines, indicated at 18.

In use of the coronary artery cutting and dilating instrument in the surgical treatment of stenotic coronary artery insufficiency, the heart will be exposed at the site of the affected coronary artery and, as illustrated in FIG. 5, a longitudinal incision will be made distal of the stenotic obstruction and spaced therefrom by a distance somewhat less than the length of the instrument cannula 12. The arterial incision will be purse-string sutured, as indicated at 19, after which the probe wire will be passed upstream into the artery through the incision to the position in which the cutting knife blade 15 will have entered the arterial stenosis S. The instrument may also be introduced proximal and passed distalward.

FIG. 6 illustrates further advancement of the instrument through the artery, causing the knife blade 15 to cut through the arterial wall at the stenosis and into the peri-arterial tissues. The depth of cut is predetermined by the particular width of the knife blade comprising the instrument. Immediately thereafter, as illustrated in FIGS. 7 and 8, the instrument is inserted further into the artery so as to place the balloon member 16 within the zone of the incised stenotic constriction, whereafter a surgical syringe 20 (partially illustrated in FIG. 7) will be actuated to force hydraulic fluid through the instrument cannula 12 and openings 17 therein to inflate the balloon. FIG. 8 illustrates how inflation of the balloon serves to dilate and spread the incised stenotic artery zone, thereby to effect immediate normal distal blood flow and pressure upon completion of the procedure. In this connection, it will be understood that, theoretically, the lumen need only be increased to a diameter of between one and two millimeters to effect such normal blood flow pressure in the stenotic or completely occluded artery. Bleeding is controlled by ligation of the purse-string suture after completion of the cutting and dilating procedure, or by ligation of a segment of vein which has been sutured circumferentially to the epicardial opening. Previous work has demonstrated in animals that if the coronary artery is longitudinally incised on its visceral surface, a new arterial wall will form. Special characteristics of the epicardium and sub-epicardial areolar tissue make this possible by containing hemorrhage from the artery. It has also been demonstrated that in the healing process, the periarterial and epicardium tissue will contain the hematoma so that a blood conduit exists immediately following the procedure. Eventually, a new vessel forms, part of which is built on the organizing hematoma.

In use of the single bladed cutting and dilating instrument of FIG. 1 as described above, the radial position of the knife blade 15 will be indicated, for example, by an indexing pin 11a projecting radially outwardly of the syringe connector fitting device 11 at a position diametrically opposed to that of said cutting blade. It is thus possible for the surgeon to know precisely the direction of the incision being made through the artery wall and into the peri-arterial tissues.

Figure 10:
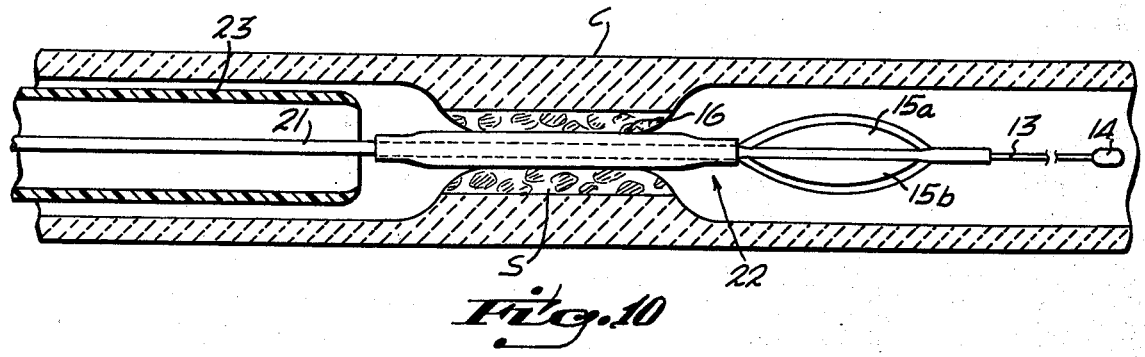
FIG. 10 illustrates the distal end portion of the peripheral artery catheter assemblage schematically illustrated in FIG. 9, showing how the cutting and dilating

While FIGS. 1, 2 and 5 through 8 illustrate a coronary cutting and dilating instrument having a single cutting blade 15, it is contemplated that a plurality of blades could also be used to bi-valve or tri-valve, selectively, the stenotic zone of an artery. FIG. 3, for example, is a partial view, on an enlarged scale, of a coronary cutting and dilating instrument which, while otherwise the same as the instrument illustrated in FIG. 1, has a pair of diametrically-opposed knife blades 15a, 15b. If the blades 15a, 15b are made shallower or of lesser radial extent, so as to cut the arterial wall but not to perforate the epicardium, the direction of the blades will be of lesser significance. This permits incision and immediate dilation of the coronary artery via a peripheral artery without the necessity of opening the chest wall of the patient in a procedure similar to that heretofore used in the decompression of stenoses by use of an inflatable balloon without cutting. As illustrated in FIGS. 9 and 10, the cannula 21 of the balloon and knife blade assemblage 22, which is otherwise the same as that of the embodiment of FIG. 1, but with two diametrically-opposed blades as illustrated in the embodiment of FIG. 3, is of such length as to permit feeding from the outside through a coronary catheter 23 introduced to the site of stenotic obstruction in a coronary artery. Thus, as illustrated by way of example in FIG. 9, the catheter 23 will be introduced through a femoral artery or some other peripheral artery and the ascending aorta into the affected coronary artery C, to terminate just short of the stenosis (see FIG. 10). Thereafter, the elongated cannula 21 with its balloon and knife blade assemblage 22 will be fed through the catheter 23 and pushed through the stenotic obstruction S, whereafter the balloon 16 will be inflated to compress the stenotic plaque and thereby open the lumen for blood flow. As illustrated in FIG. 9, the external end of the catheter 23 will be provided with appropriate fittings for connection with surgical syringe 20a for hydraulic inflation of the dilating balloon 16, and for introduction of medical fluid through an auxiliary surgical syringe 20b. In this procedure, it will be understood that, ordinarily, the instrument blades 15a, 15b will be shallow enough not to cut through the arterial wall at the stenosis, while nevertheless "valving" the stenotic mass to facilitate smooth introduction of the balloon 16 through the approximate center of the stenosis. In this connection, it will be understood that a plurality of symmetrically opposed knife blades will preferably be employed in this procedure. Thus, while two diametrically-opposed, shallow knife blades 15a, 15b are illustrated in FIG. 10, it is contemplated that three, or even four or more symmetrically arranged blades can also be used to effect longitudinal cutting of the stenotic obstruction prior to the introduction and dilation of the inflating balloon 16.

While there is illustrated and described herein only two forms in which the invention can conveniently be embodied in practice, it is to be understood that these embodiments are presented by way of example only and not in a limiting sense. The invention, in brief, comprises all embodiments and modifications coming within the scope and spirit of the following claims.

What is claimed is:

1. A coronary dilating and cutting instrument comprising, in combination, a cannula, flexible probe means extending outwardly of one end of said cannula for the guidance thereof through an artery, cutting means extending laterally outwardly of said cannula for longitudinally cutting a stenonic arterial zone as said cannula is introduced centrally through the artery, said cutting means being located behind said flexible probe means and comprising a flat knife blade defining a radially-extending plane with respect to said cannula, said knife blade having a cutting edge of arcuate shape, an elongated, tubular, inflatable balloon circumjacent said cannula directly behind said cutting means and having end portions thereof circumferentially secured and hermetically sealed with respect to spaced, outer surface portions of said cannula, through opening means in said cannula side wall and in registration with said balloon for the introduction of hydraulic fluid into said balloon through the other end of said cannula, and means at the other end of said cannula for connection with a source of hydraulic fluid under pressure for the controlled inflation of said balloon.

2. A coronary dilating and cutting instrument as defined in claim 1 wherein said flexible probe means comprises a length of resilient wire terminating in blunt tip.

3. A coronary dilating and cutting instrument as defined in claim 2 wherein the proximate end of said resilient wire is coaxially received within said one end of said cannula for attachment thereto and for blockage of said cannula at said one end.

4. A coronary dilating and cutting instrument as defined in claim 1 wherein said cutting means comprises a plurality of radially-extending knife blades symmetrically spaced about said cannula, the cutting edge of each knife blade of which is of arcuate shape.

5. A coronary dilating and cutting instrument as defined in claim 4 and further including a coronary catheter the internal diameter of which is of sufficient size to permit the passage therethrough of said cannula, said probe means, said cutting means, and said inflatable balloon when in its collapsed condition, whereby said cannula can be fed through said catheter at its proximate end outside the body of the patient for placement at the site of a stenotic obstruction through a catheterized artery.

6. A coronary dilating and cutting instrument as defined in claim 1 including index means at the other end of said cannula for indicating the relative radial direction of said knife blade.

* * * * *